United States Patent [19]

Bauer et al.

[11] Patent Number: 4,693,750

[45] Date of Patent: Sep. 15, 1987

[54] DIRECT TABLETTING AGENT

[75] Inventors: Kurt H. Bauer, Freiburg; Bernd Pritzwald-Stegmann; Werner Luft, both of Reitmehring, all of Fed. Rep. of Germany

[73] Assignee: Meggle Milchindustrie GmbH & Co. KG., Wasserburg, Fed. Rep. of Germany

[21] Appl. No.: 831,598

[22] Filed: Feb. 21, 1986

[30] Foreign Application Priority Data

Feb. 22, 1985 [DE] Fed. Rep. of Germany ....... 3506276

[51] Int. Cl.$^4$ ................................................. A61K 9/20
[52] U.S. Cl. ................................ 106/163.1; 514/480; 514/781; 427/3
[58] Field of Search ....................... 106/163.1; 424/35; 427/3; 514/781, 480

[56] References Cited

U.S. PATENT DOCUMENTS

| 3,185,626 | 5/1965 | Baker | 427/3 |
| 4,316,884 | 2/1982 | Alam et al. | 424/35 |
| 4,423,086 | 12/1983 | Devos et al. | 427/3 |
| 4,432,966 | 2/1984 | Zeitoun et al. | 424/35 |
| 4,511,553 | 4/1985 | Boesig et al. | 424/35 |

FOREIGN PATENT DOCUMENTS

| 45-5275 | 2/1970 | Japan | 514/781 |
| 48-32645 | 10/1973 | Japan | 427/3 |
| 50-35323 | 4/1975 | Japan | 514/781 |
| 55-35047 | 3/1980 | Japan | 514/781 |

Primary Examiner—Ronald W. Griffin
Attorney, Agent, or Firm—Felfe & Lynch

[57] ABSTRACT

The present invention provides a direct tabletting agent, consisting essentially of lactose and cellulose with a ratio of lactose to cellulose, referred to the weight, of from 95 to 40:5 to 60, the lactose being present partly in crystalline and partly in amorphous form and the cellulose being present as finely-divided powder.

The present invention also provides processes for the production of this direct tabletting agent.

16 Claims, 1 Drawing Figure

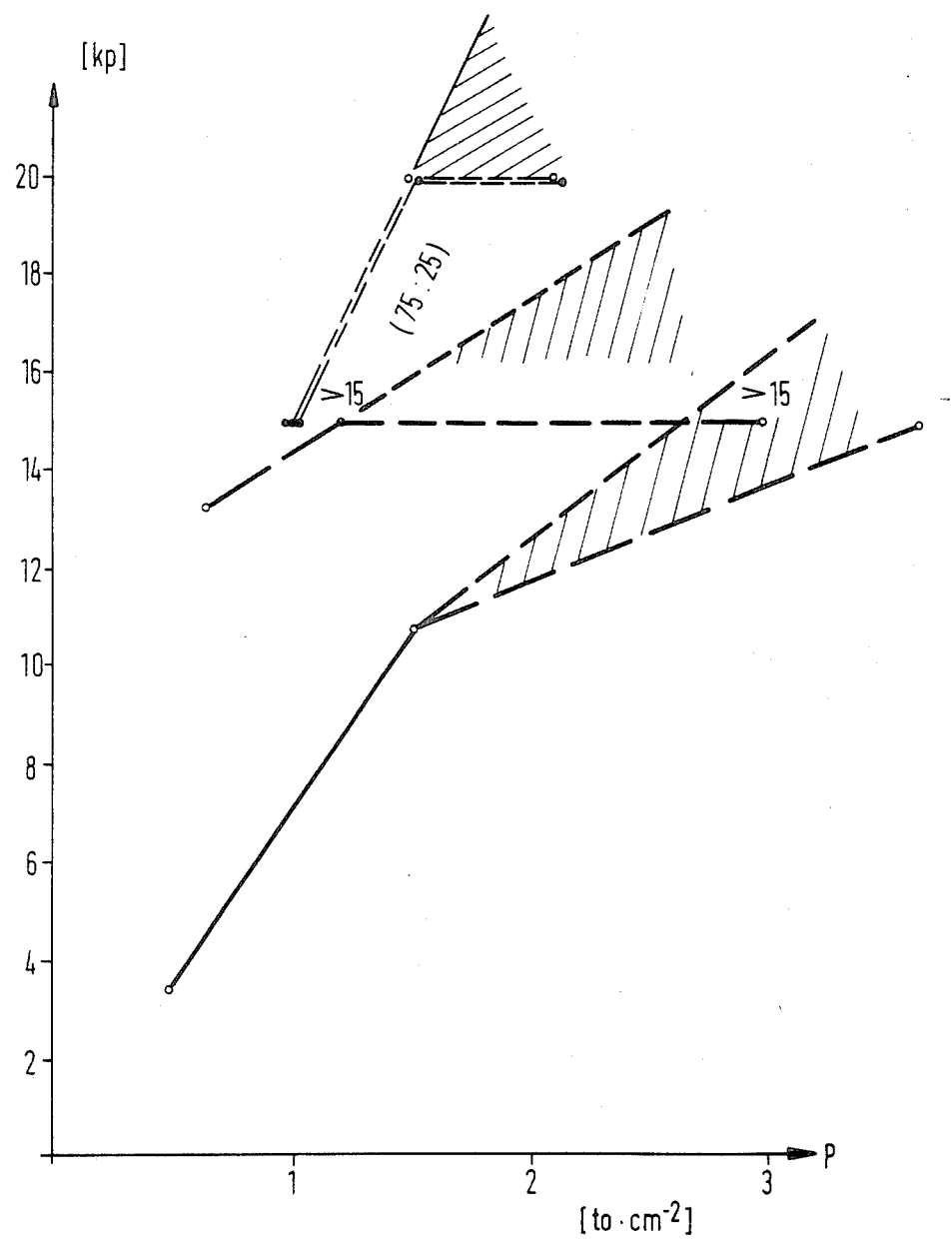

DIRECT TABLETTING AGENT

The present invention is concerned with a direct tabletting agent and with a process for the production thereof.

Various processes are known for the production of tablets, direct tabletting being especially desirable. For this purpose, a pharmaceutically active material is mixed with a carrier material and tabletted directly. This process is especially simple since it does not require any intermediate steps for the production of a core or granulate. However, many of the known carrier materials are not suitable for direct tabletting. The carrier material must possess not only a good flowability but also a good compressability at a low pressure. The pressed bodies must have a high degree of hardness and wear resistance but, at the same time, they must disintegrate quickly upon contact with gastric juices. At the moment, these requirements are substantially fulfilled by microcrystalline cellulose, which is used as adjuvant for direct tabletting. However, a disadvantage of microcrystalline cellulose is that it is difficult to produce and, therefore, is also expensive and not very economical.

Therefore, it is an object of the present invention to provide an agent for direct tabletting which, on the one hand, fulfils the requirements which are demanded of such a material but, on the other hand, is more cost favourable than the expensive microcrystalline cellulose.

Thus, according to the present invention, there is provided a direct tabletting agent, consisting essentially of lactose and cellulose with a ratio of lactose to cellulose, referred to the weight, of from 95 to 40:5 to 60, the lactose being present partly in crystalline and partly in amorphous form and the cellulose being present as finely divided powder.

The agent according to the present invention is very well suited for direct tabletting. It has excellent flow properties and pressed bodies produced therefrom are very hard and disintegrate quickly.

As stated above, the direct tabletting agent according to the present invention consists essentially of lactose and cellulose, the ratio of lactose to cellulose, referred to the weight, being from 95 to 40 parts of lactose to 5 to 60 parts of cellulose. If the agent contains more than 95% lactose, then tablets formed therefrom are not hard enough. The use of more than 60% cellulose is uneconomic since a further improvement of the properties is no longer achieved. The ratio of lactose to cellulose is preferably 80 to 65 parts lactose to 20 to 35 parts cellulose, a mixture of 75 parts lactose and 25 parts cellulose being especially preferred.

It is important that the lactose in the direct tabletting agent according to the present invention is present partly in crystalline and partly in amorphous form. The combination of lactose in crystalline and amorphous form and of finely divided cellulose results in the good properties of the agent according to the present invention.

Conventional additives can also be added to the direct tabletting agent according to the present invention. As conventional additives, there can be used the disintegration agents, aromatising agents, stabilizers, filling agents, colouring materials and/or lubricants conventionally employed in the production of tablets.

According to a first method for the production of the direct tabletting agent according to the present invention, cellulose powder is mixed with a hot solution of, for example, 50 to 60% lactose in water, the mixture is cooled and the mass obtained is granulated and subsequently dried.

The hot lactose solution preferably has a temperature of from 60° to 100° C., a temperature of the lactose solution of from 90° to 95° C. being especially preferred.

The drying of the granulated mass can be carried out by means of conventional drying processes, drying in a fluidized bed being preferred.

The cellulose used is a very fine cellulose powder of pharmacopoeia standard, cellulose with a particle size of less than 100 μm. being preferred. The use of microcrystalline cellulose is not necessary but is, nevertheless, possible.

According to a further method, the direct tabletting agent according to the present invention can be produced by mixing microcrystalline lactose with cellulose powder in a ratio of 95 to 40 parts by weight of lactose to 5 to 60 parts by weight of cellulose powder, slurrying the mixture in cold water and subsequently spray drying.

As microcrystalline lactose, there is hereby to be understood a lactose with a particle size of less than 100 μm. A lactose is preferably used, the crystals of which preponderantly have a particle size of less than 50 μm. A lactose is especially preferred, the crystals of which preponderantly have a particle size of less than 32 μm.

As cellulose, there is again used a very finely powdered cellulose according to pharmacopoeia standards, a cellulose being preferred with a particle size of less than 100 μm. The use of microcrystalline cellulose is not necessary but is, nevertheless, possible.

With the direct tabletting agent according to the present invention, tablets can be produced which have a great hardness and disintegrate quickly. Surprisingly, tablets produced from the direct tabletting agent according to the present invention have, in the case of a given pressing force, a greater degree of hardness than pressed bodies which are produced from finely powdered cellulose or from microcrystalline cellulose.

FIG. 1 of the accompanying drawings is a graphic illustration in which the hardness of pressed bodies made from finely powdered cellulose, microcrystalline cellulose and the direct tabletting agent according to the present invention are plotted against the pressing force. It can clearly be seen from this FIGURE that, with the tabletting agent according to the present invention, especially hard pressed bodies can be obtained especially at the desired average pressing force.

The following Examples are given for the purpose of illustrating the present invention:

EXAMPLE 1

880 kg. cold water, 358.3 kg. finely crystalline lactose, 95% of the particles of which have a size of less than 32 μm., and 125 kg. powdered cellulose are so mixed in an appropriate container that to the water present therein there is first added the lactose and thereafter the cellulose and the whole is then well mixed for some minutes. Subsequently, the slurry obtained is sprayed into a drying tower to which is supplied air with a temperature of about 150° C. The dried product can be used directly.

EXAMPLE 2

Cellulose powder is mixed with a hot solution of 50% lactose in water, the mixture is allowed to cool and the mass obtained is granulated and subsequently dried. The mass obtained contains 75% lactose and 25% cellulose. The sieve analysis of the product is:

particles >500 μm.: 24.2%; 400 to 500 μm.: 14.6%; 315 to 400 μm.: 12.0%; 200 to 315 μm.: 13.8%; 100 to 200 μm.: 23.2%; <100 μm.: 12.0%.

Tablets are pressed with a pressing force of:
I: 1.0 t/cm²
II: 1.5 t/cm²
III: 2.2 t/cm².

The tablets obtained have a hardness of:
I: 5.0 kp
II: 9.2 kp
III: 14.4 kp

The speed of disintegration of the tablets in water at 37° C. is:
I: 34 seconds
II: 215 seconds
III: 18 minutes

EXAMPLE 3

Tablets are produced from a direct tabletting agent of 75% lactose and 25% cellulose produced by spray drying. The pressing forces used are:
I: 1.0 t./cm²
II: 1.5 t./cm²
III: 2.1 t./cm²

The tablet hardness of the pressed bodies is:
I: 15 kp
II: more than 20.0 kp
III: more than 20.0 kp.

The speed of disintegration of the tablets in water at 37° C. is:
I: about 15 minutes
II and III about one hour.

EXAMPLE 4

Tablets are pressed from microcrystalline cellulose, from fine cellulose powder, from lactose and from a direct tabletting agent according to the present invention containing 75% lactose and 25% cellulose. The results obtained are set out in the following Table:

TABLE

|  | comparisons | | | according to |
| --- | --- | --- | --- | --- |
|  | micro-cryst. cellulose | powdered cellulose | lactose D 80 | the invention 75% lactose 25% cellulose |
| sieve analysis (g) | | | | |
| >800 (μm) | | 0.1 | | |
| 630–800 | | 0.3 | | |
| 500–630 | | 0.3 | 0.2 | |
| 400–500 | | 0.3 | 1.0 | |
| 315–400 | 0.1 | 0.7 | 26.0 | |
| 200–315 | 4.7 | 2.9 | 35.5 | 16.2 |
| 100–200 | 28.7 | 33.9 | 23.7 | 30.4 |
| <100 | 66.6 | 61.6 | 13.8 | 53.4 |
| pressing force (t/cm²) | | | | |
| I | 0.63 | 0.48 | 0.25 | 1.1 |
| II | 1.20 | 1.48 | 1.50 | 1.6 |
| III | 2.98 | 4.08 | 4.40 | 2.2 |
| tablet hardness (kp) | | | | |
| I | 13.3 | 3.5 | 0.5 | 8.4 |
| II | 15.0 | 10.8 | 1.5 | 15.4 |
| III | 15.0 | 15.0 | 5.0 | 18.8 |
| tablet disintegration (H₂O/37° C.) | | | | |
| I | 2 min 23 sec | 15 min | 23 sec | 19 sec |
| II | 14 min 30 sec | 15 min | 25 sec | 2 min 4 sec |
| III | 15 min | 15 min | 60 sec | 13 min 30 sec |

The comparisons show that, with the tabletting agent according to the present invention, tablets are obtained, the hardness of which is comparable with that of tablets made from microcrystalline cellulose and that the speed of dissolving thereof is very good.

We claim:

1. A direct tabletting agent, consisting essentially of a mixture of lactose and cellulose with a ratio of lactose to cellulose by weight, of from 95 to 40:5 to 60, the lactose being present partly in crystalline and partly in amorphous form and the cellulose being present as finely-divided powder and a conventional additive selected from the group consisting of a disintegration agent, an aromatising agent, a stabilizer, a filling agent, a coloring material, a lubricant and a combination thereof or said mixture of lactose and cellulose without the conventional additive.

2. The direct tabletting agent of claim 1, wherein the weight ratio of lactose to cellulose is from 65 to 80:35 to 20.

3. The direct tabletting agent of claim 2 wherein the cellulose has a particle size of less than 100 um.

4. The direct tabletting agent of claim 1 wherein the cellulose has a particle size of less than 100 um.

5. The direct tabletting agent of claim 1 containing at least one disintegration agent, aromatising agent, stabilizer, filling agent, colouring material and/or lubricant.

6. The direct tabletting agent of claim 1 consisting essentially of said mixture of lactose and cellulose.

7. The direct tabletting agent of claim 1 consisting essentially of said mixture of lactose and cellulose and said conventional additive.

8. A process for the production of a direct tabletting agent, comprising mixing cellulose powder with a hot solution of 50 to 60% lactose in water, allowing the mixture to cool to obtain a solid mass from the solution; and granulating and drying the mass.

9. The process of claim 8, wherein the hot lactose solution has a temperature of from 60° to 100° C.

10. The process of claim 9, wherein the hot lactose solution has a temperature of from 90° to 95° C.

11. The process of claim 8 wherein there is added to the mixture of lactose and cellulose at least one disintegration agent, aromatising agent, stabilizer, filling agent, colouring material and or lubricant.

12. A process for the production of a direct tabletting agent, comprising slurrying a mixture of microcrystalline lactose and cellulose powder in a weight ratio, of 95 to 40:5 to 60 in cold water and subsequently spray drying the slurry.

13. The process of claim 12, wherein the microcrystalline lactose has a particle size of less than 100 um.

14. The process of claim 13, wherein the microcrystalline lactose has a particle size of preponderantly less than 50 um.

15. The process of claim 14, wherein the microcrystalline lactose has preponderantly particles of a size of less than 32 um.

16. The process of claim 12 wherein the cellulose has a particle size of less than 100 um.

* * * * *